United States Patent [19]

Lee et al.

[11] Patent Number: 4,575,452

[45] Date of Patent: Mar. 11, 1986

[54] KIT FOR SILVER STAINING PROTEINS AND NUCLEIC ACIDS

[75] Inventors: Duk H. Lee, Wellesley; Thomas J. O'Connell, III, Quincy, both of Mass.

[73] Assignee: E. I. Du Pont de Nemours and Company, Wilmington, Del.

[21] Appl. No.: 652,890

[22] Filed: Sep. 21, 1984

[51] Int. Cl.$^4$ .............................................. G01N 33/68
[52] U.S. Cl. ...................................... 422/61; 430/454; 430/455; 430/456; 436/86; 436/94; 436/174; 436/905
[58] Field of Search .................... 436/86, 87, 88, 94, 436/164, 169, 174, 175, 176, 515, 905; 422/61; 430/413, 454, 455, 456

[56] References Cited

U.S. PATENT DOCUMENTS

| | | | |
|---|---|---|---|
| 2,548,552 | 4/1951 | Muehler | 430/454 X |
| 2,696,439 | 12/1954 | Levinos et al. | 430/454 X |
| 3,326,685 | 6/1967 | Abbott et al. | 430/454 X |
| 3,622,332 | 11/1971 | Kane | 430/455 X |
| 4,405,720 | 9/1983 | Merril | 436/86 |
| 4,416,998 | 11/1983 | Adams et al. | 436/86 |
| 4,434,234 | 2/1984 | Adams et al. | 436/86 |
| 4,459,356 | 7/1984 | Gersten et al. | 436/86 |
| 4,468,466 | 8/1984 | Morrissey | 436/86 |

FOREIGN PATENT DOCUMENTS 0631184 10/1949 United Kingdom ............... 430/455

OTHER PUBLICATIONS

Analytical Biochemistry, Oakley et al., vol. 105, p. 361 (1980).

Primary Examiner—Barry S. Richman
Assistant Examiner—Robert J. Hill, Jr.

[57] ABSTRACT

A method and kit for the optical detection of proteins and nucleic acids in a matrix, such as polyacrylamide electrophoresis gels. The method comprises fixing the proteins and nucleic acids in the matrix using aromatic sulfonic acids having tertiary amines capable of forming coordination complexes with silver ion.

3 Claims, No Drawings

KIT FOR SILVER STAINING PROTEINS AND NUCLEIC ACIDS

TECHNICAL FIELD

The present invention relates to a method for visualizing a protein or nucleic acid contained in a matrix, particularly an electrophoresis matrix such as polyacrylamide.

BACKGROUND OF THE INVENTION

Electrophoresis is a well known analytical technique in biochemistry. A sample is placed in a matrix and exposed to an electric field which causes various components in the sample to migrate within the matrix at didferent rates depending on the component's charge, molecular weight and other physical and chemical properties. After migration has occurred, the resulting migration pattern is ascertained. Various methods to ascertain the migration pattern have been developed. These include autoradiography and staining for visual or densitomeric determination. Typical stains include the dyes Coomassie Brilliant Blue and Ponceau S. Silver staining has been used to increase sensitivity over that provided by dyes. A widely used silver staining technique is that described by Merril et al., Methods in Enzymology, Volume 96, p. 230 (1983). An electrophoresis matrix, specifically polyacrylamide, is immersed in either an acid or an acid/alcohol solution for about one hour to fix the protein in the matrix. The matrix is then washed, typically for thirty minutes. The matrix is then soaked for about five minutes in a dichromic acid solution to oxidize the protein. Next, the gels are soaked in a silver nitrate solution for twenty minutes and then rinsed with a sodium carbonate/formaldehyde buffer to reduce silver ion bound to proteins and nucleic acids. A silver pattern is then allowed to develop. Development is stopped with acetic acid. The pattern is then analyzed either by direct visualization or by instrumental techniques.

The method of Merril et al. was simplified by Oakley et al. ([Analytical Biochem., Volume 105, p. 361 (1980)]. Electrophoresis gels were treated with unbuffered glutaraldehyde to cross-link proteins. Following rinsing, the gels were treated with ammoniacal silver solution. A combination of citric acid and formaldehyde was used to reduce silver ion to silver.

It has been found that the sensitivity of the silver staining technique for the optical detection of proteins and nucleic acids can be improved substantially if the matrix is treated with a fixing agent comprising a highly aromatic compound having at least one sulfonic acid group and at least one aromatic, tertiary amine, preferably as part of an oxazole group. Preferred compounds are selected from the group consisting of

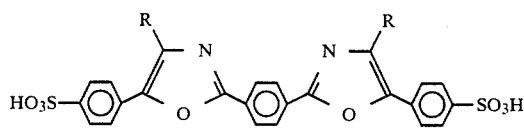

wherein R is H, $CH_3$, $C_2H_5$ or $CH_2N^+(CH_3)_3$,

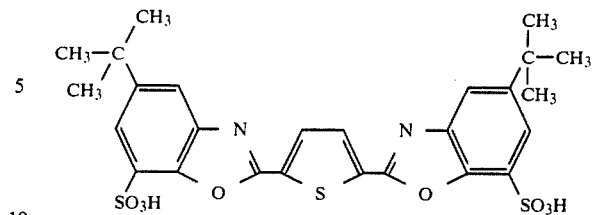

and

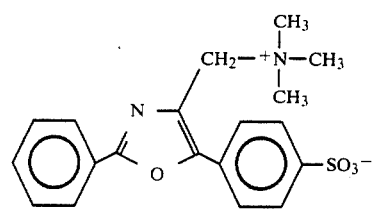

Optionally, the matrix is treated with a sensitizing agent selected from the group consisting of sodium sulfide, dithiothreitol, thiourea and sodium thiosulfate.

In addition, the sensitivity of the silver staining technique for the optical detection of nucleic acids can be improved substantially if the matrix is treated with a fixing agent comprising a compound of the formula:

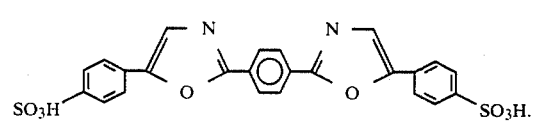

The increase in sensitivity for both protein and nucleic acids is believed to result from the ability of these fixing agents to cross-link proteins and nucleic acids while, at the same time, providing an aromatic ring containing a tertiary amine which is capable of forming a coordination complex with silver.

SUMMARY OF THE INVENTION

In a first aspect, the present invention is a method for detecting a protein or nucleic acid in a matrix, comprising:

(a) contacting the matrix with a fixing agent selected from the group consisting of

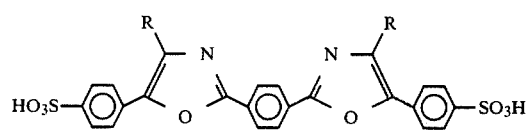

wherein R is H, $CH_3$, $C_2H_5$ or $CH_2N^+(CH_3)_3$,

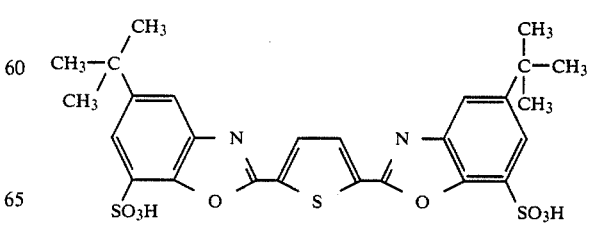

and

-continued

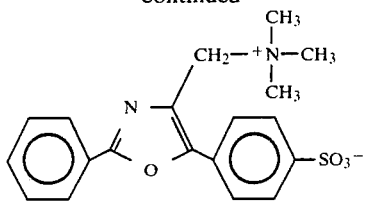

(b) optionally contacting the matrix with a sensitizing agent selected from the group consisting of sodium sulfide, thiourea, dithiothreitol and sodium thiosulfate, (c) contacting the matrix with silver ion, and (d) contacting the matrix with a developer capable of reducing silver ion to metallic silver.

The present invention also comprises a kit for the optical detection of proteins and nucleic acids comprising the fixer, sensitizing agent, source of silver ions, and developer of steps (a)–(d) and further including a stopper capable of stopping reduction of silver ions to metallic silver.

In a second aspect, the present invention is a method for detecting a nucleic acid in a matrix, comprising:

(a) contacting the matrix with an intercalating agent comprising a compound of the formula

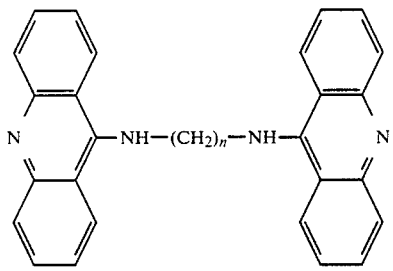

wherein n is an integer from 3 to 10, (b) contacting the matrix with a washing agent to remove excess intercalating agent, (c) contacting the matrix with silver ion, and (d) contacting the matrix with a developer capable of reducing silver ion to metallic silver.

DETAILED DESCRIPTION OF THE INVENTION

Techniques for electrophoretically separating protein and nucleic acids in a matrix are well known. A particularly preferred matrix is polyacrylamide gel. Other matrices include paper, agarose, nitrocellulose, etc. The present method is not limited to the optical detection of proteins and nucleic acids in electrophoresis matrices, but can be used to measure protein and nucleic acid patterns in other matrices such as those used in thin layer chromatography.

For the optical detection of proteins and nucleic acids, the matrix is immersed in a solution containing a fixing agent selected from the group consisting of compounds of the formulae:

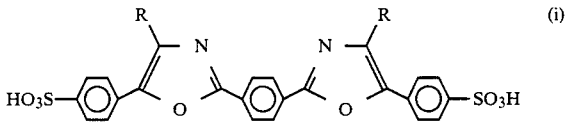

wherein R is H, $CH_3$, $C_2H_5$ or $CH_2N^+(CH_3)_3$,

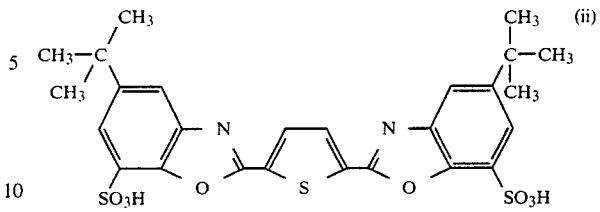

and

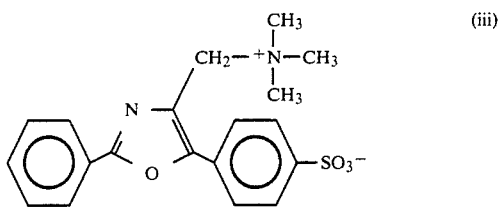

Compound (i) of the formulae above is preferred and will be referred to hereinafter as POPOP-disulfonic acid. A preferred solution comprises 0.05% (w/v) of POPOP-disulfonic acid in 50% methanol, 12% acetic acid and 38% distilled water by volume. Incubation time is determined empirically and depends primarily on the thickness of the matrix. For example, for a polyacrylamide matrix of dimensions $14 \times 16 \times 0.15$ cm, the optimum fixing time is about forty five minutes with constant agitation.

Next, the matrix can be immersed in a sensitizing solution. The sensitizing solution contains a compound selected from the group consisting of dithiothreitol, thiourea, sodium thiosulfate and sodium sulfide. The preferred compound is dithiothreitol. A preferred solution comprises 5 ng/mL of dithiothreitol in distilled water. Typical incubation for the previously described matrix is about fifteen minutes.

Next, the matrix is immersed in a silver nitrate solution, generally 0.1% silver nirate in distilled water. The matrix is incubated with agitation for about thirty minutes.

Next, the protein or nucleic acid pattern in the matrix is developed. In general, the matrix is washed quickly in distilled water and rinsed quickly in developer solution. The developer is a basic buffer solution whose pH is between 11 and 12 and which contains formaldehyde. Preferred buffers are sodium carbonate and sodium phosphate, the latter being most preferred. A preferred solution is 3% (w/v) sodium carbonate or 0.5% (w/v) sodium phosphate and 0.5 mL formaldehyde (37% by weight) per liter of distilled water. The matrix is then rinsed again with the developer solution. Finally, the matrix is developed for about five minutes to an hour in the developer solution. The optimum time depends upon the extent of sample loading and background staining attributable to matrix characteristics.

Finally, the reaction in the matrix is stopped by lowering the pH of the developer to about 3 in the case of a carbonate-based developer, or 7 for a phosphate-based developer. A convenient method comprises the addition of citric acid directly to the developer solution.

The present invention differs from the prior art in that the first step, fixing, leads to a chemical interaction between amino groups present in the protein molecules and sulfonic acid groups in the POPOP-disulfonic acid or other fixing agent. Precipitation of basic and neutral amino acids by aromatic mono-sulfonic acids has been reported. [Suida, W., Z. Physiol. Chem. 50, 174, (1906)]. The aromatic sulfonic acids are sufficiently strong acids that they may be expected to form salts with all types of amino acids. It apparently has not been recognized generally that many of the sulfonic acid salts of the neutral or basic proteins are sparingly soluble. The amino groups in the protein molecule form coordination complexes with metals such as silver. However, when the amino groups in protein interact with sulfonic acids, the ability of nitrogen atoms to complex with metal ions is lost. But if the aromatic sulfonic acid itself contains amino groups, the coordinating property of the protein sulfonic acid salts is not affected.

Most of the polyamino aromatic sulfonic acid derivatives are either black or very dark colored materials and find little use in silver staining procedure. The sulfonic acids disclosed herein are either yellow or brown colored in the solid state. However, dilute solutions used in the fixing step are colorless. The process of chemical interaction leading to insoluble salt formation gives this present process its sensitivity advantage over other silver staining methods, particularly for low molecular weight proteins.

Silver complexed with protein is more readily reduced in the presence of sulfur. Thiourea and its derivatives are strongly adsorbed to the surface of silver halides, then decompose to form sulfide. [James, T. H. and Vanselow, W., J. Photo. Sci 1, 133, (1953)]. Sodium thiosulfate is also known to act as a sensitizer. [Wood, H. W., J. Phot. Sci. 2, 154, (1954)]. The silver deposited on the protein or nucleic acid in the matrix is more easily reduced due to the presence of the sulfur containing compounds. It is believed that the silver sulfide acts as a catalyst for the reduction of silver ions. Sodium sulfide, thiourea, dithiothreitol and sodium thiosulfate in 0.01 to 0.05% concentration can be used to sensitize silver ion.

The preparation of suitable fixing agents used in accordance with the present invention is described below.

(I) Preparation of 4,4'-[1,4-phenylenebis(2,5-oxalediyl)]-bisbenzenesulfonic acid (POPOP-disulfonic acid)

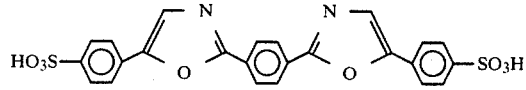

POPOP-disulfonic acid is prepared by the sulfonation of POPOP [1,4-bis(5-phenyloxazole-2-yl)-benzene] with fuming sulfuric acid as described below.

One hundred milliliters of 20% fuming sulfuric acid (oleum) is charged into a 500 mL flask. Stirring is begun, and 50.0 g of POPOP is added in small portions. The reaction is exothermic. After the addition is complete, the reaction mixture is heated at about 90°-100°C. with stirring for two hours. The reaction is then quenched by pouring the reaction mixture onto 500 g of crushed ice with stirring. A bright-yellow product precipitates as a very fine powder. The resulting suspension is allowed to stand overnight. The product is then collected on a medium-porosity fritted-glass Buchner funnel. It should not be washed at this point, nor should the filter cake be disturbed. As much liquid is removed from the filter cake as possible. The pasty filter cake is then washed by stirring it in 200 mL of 2/1 (v/v) water/methanol or 1/20/10 concentrated hydrochloric acid/water/methanol. Water alone should not be used, as a very thick paste will form. Stirring is continued until the product is finely dispersed. The suspension is then allowed to settle briefly, and the solid is collected by vacuum filtration. The washing process should be repeated once. The product is then dried in a vacuum oven at 60°-70° C. Typical yields are 67-73 g (90-94%).

(II) Preparation of 4,4'-[1,4-phenylenebis(4-methyl-2,5-oxazolediyl)]-bisbenzenesulfonic acid (dimethyl-POPOP-disulfonic acid)

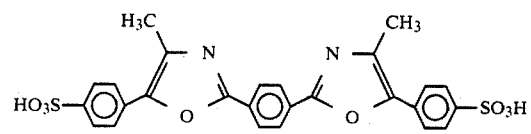

Dimethyl-POPOP-disulfonic acid is prepared by the sulfonation of dimethyl POPOP with fuming sulfuric acid by using the same procedure for the preparation of POPOP-disulfonic acid.

(III) Preparation of 2,2'-(2,5-thiophenediyl)bis[5-(1,1-dimethylethyl)-7-benzoxazole-sulfonic acid](BBOT-disulfonic acid)

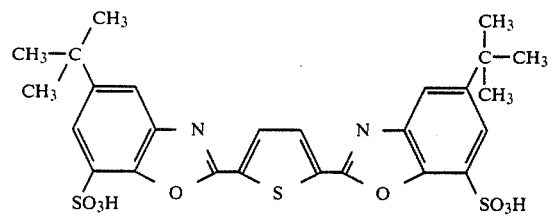

BBOT-disulfonic acid is prepared by the sulfonation of BBOT [2,5-bis(5-t-butyl-2-benzoazolylthiophene)] with fuming sulfuric acid as described below.

One hundred milliliters of 20% fuming sulfuric acid is charged into a 500 mL Erlenmeyer flask. With magnetic stirring, 60 g of BBOT is added in small portions. The reaction is exothermic. After the addition is complete, the reaction mixture is heated to 90°-100° C. for two hours. The reaction is then quenched by pouring the reaction mixture onto 500 g of crushed ice. A brown product precipitates as a fine powder. The product is collected on a fritted-glass Buchner funnel. The product is then washed by stirring it in 200 mL of 1N hydrochloric acid. Washing is prepared several times. The product is then dried in a vacuum oven at 60°-70° C. Typical yields are 75-80 g (89-93%).

(IV) Preparation of N,N,N-Trimethyl-2-phenyl-5-(4-sulfophenyl)-4-oxazolemethanamonium hydroxide (inner salt)

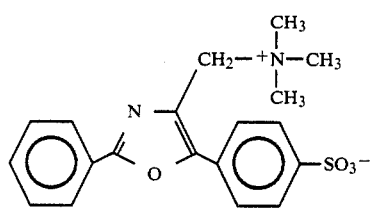

One hundred grams (613 mM) of isonitrosopropiophenene (Eastman Organic Chemicals) and 65 grams (613 mM) of benzaldehyde were dissolved in glacial acetic acid. Hydrogen chloride gas as bubbled through the solution with stirring until a yellow precipitate was formed. The precipitate was collected and washed with ether until it was white. This product as dissolved in methanol with heating and neutralized with sodium hydroxide. The product, 2,5-diphenyl-4-methyloxazole-N-oxide, was dissolved in ethanol, placed in a Paar hydrogenation bottle with freshly activated Raney-nickel catalyst and degassed by vacuum. The system was then charged to a pressure of about 3 atmospheres with hydrogen gas. The reaction was continued with supplemental hydrogen being added until hydrogen was no longer consumed and thin layer chromatography using 8:1 hexane/ethyl acetate on silica gel showed no starting material. The catalyst was filtered, the solvent distilled, and the resulting white crystals of 2,5-diphenyl-4-methyloxazole were dried in a vacuum oven. Yield was 110 g (80%).

Fifty grams of 2,5-diphenyl-4-methyloxazole (0.21 moles) was dissolved in 250 mL of carbon tetrachloride. A catalytic amount (about 25 mg) of benzoyl peroxide was added, and the solution was heated to reflux. Sulfuryl chloride (17 mL; 0.21 moles) was added dropwise to the refluxing mixture, and refluxing was continued for about an hour. The mixture was allowed to cool to room temperature. The solvent was removed under reduced pressure, and the remaining product, 4-chloromethyl-2,5-diphenyloxazole, was recrystallized from ethanol. Yield was 47 g (80%); melting point 138°–139° C.

Sixty milliliters of 20% fuming sulfuric acid was charged into a 250 mL flask. With stirring, 40 grams of 4-chloromethyl-2,5-diphenyloxazole was added in small portions. The reaction is exothermic. After the addition was completed, the reaction mixture was heated at 90°–100° C. for two hours. The reaction was then quenched by pouring the reaction mixture onto 300 g of crushed ice with stirring. The product precipitated as a fine powder. The resulting suspension was allowed to stand overnight. The product was then filtered on a medium porosity fritted-glass Buchner funnel. The precipitate was washed with 1/1 (v/v) water/methanol. The product, 4-chloromethyl-2-phenyl-5-(4-sulfophenyl)oxazole, was then dried in a vacuum oven at 60°–70° C. Yield was 40 g (80%); melting point >300° C.

Into 500 mL of ethanol was stirred 20.6 g (56 mM) of 4-chloromethyl-2-phenyl-5-(4-sulfophenyl)oxazole. Trimethylamine was bubbled into the stirred solution. At first, all the material went into solution, then a white precipitate began to form. Bubbling of trimethylamine into the reaction mixture was continued until thin layer chromatography using 1:1 methanol/ethyl acetate (v/v) on silica gel showed no starting material. The precipitate was collected and washed with ethanol. Yield was 17.0 g (83%).

(V) Preparation of 2,2'-(1,4-phenylene)bis[N,N,N-trimethyl-5-(4-sulfophenyl)]-4-oxazole methanaminium dihydroxide, (bis inner salt)

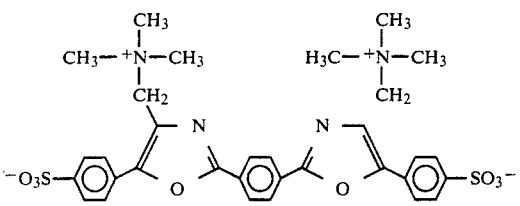

In 500 mL of carbon tetrachloride, 23 g (60 mM) of 1,4-bis(4-methyl-5 phenyloxazol-2-yl)benzene was dissolved. A catalytic amount of benzoyl peroxide was added, and the solution was heated to reflux. Sulfuryl chloride (10 mL; 63 mM), dissolved in 10 mL of carbon tetrachloride, was added dropwise to the refluxing solution. The refluxing was continued for about 4 hours. After the addition of the sulfuryl chloride was completed, the mixture was allowed to cool to room temperature overnight. The precipitated product was collected by filtration and recrystallized from methylene chloride. Yield was (18.7 g; 65%). TLC using 1:8 acetone/chloroform showed no starting material, but several small spots.

1,4-Bis(4-chloromethyl-5-phenyloxazol-2-yl)benzene (18.7 g; 40 mM) was added in small portions to 75 mL of 20% fuming sulfuric acid with stirring. The reaction as exothermic. After the addition, the reaction mixture was heated at about 95°–110° C. The reaction was then quenched by pouring the reaction mixture onto 200 g crushed ice. The yellowish brown precipitate was allowed to stand overnight. The product was then collected on a fritted-glass Buchner funnel and washed several times with water. The product was then dried in a vacuum oven at 60°–70°. Yield was 12 g (60%).

For the optical detection of nucleic acids in a matrix, the matrix is immersed in a solution containing an intercalating, cross-linking reagent of the formula:

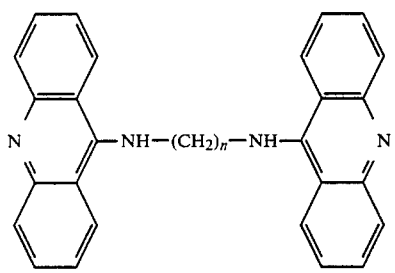

wherein n is an integer from 3 to 10.

A preferred solution comprises 0.05% of the reagent, 50% (v/v) methanol, 12% (v/v) acetic acid and water. Incubation time is determined empirically. For a polyacrylamide matrix of dimensions 14×16×0.15 cm, the matrix is incubated for about 45 minutes with agitation.

Next, the matrix is washed in a solution comprising 10% (v/v) ethanol and 5% (v/v) acetic acid in water. The matrix is incubated in the solution for about 15 minutes with agitation.

Next, the matrix is washed in distilled water with agitation for about 15 minutes. The matrix is washed with fresh water two additional times.

Next, the matrix is incubated in a silver nitrate solution. A preferred solution comprises 0.1% $AgNO_3$ in distilled water. Typical incubation time is 30 minutes.

Next, the nucleic acid pattern is developed by washing the matrix quickly in distilled water; rinsing the matrix in a developer solution comprising typically 3% $Na_2CO_3$ and 0.5 mL formaldehyde per liter of distilled water; rinsing again in developer; and, finally immersing the matrix in developer for five minutes to an hour depending on nucleic acid loading and background staining.

Finally, the development is stopped by lowering the pH of the developer solution to about 3. A convenient method comprises the addition of a solution of citric acid in distilled water directly to the developer solution. A preferred solution for use with the developer solution described above is 2.3M citric acid.

It was recognized that the acridine derivative proflavine binds to double-stranded DNA primarily by intercalation of the aromatic chromophore between the base pairs. [Lerman, L. S., J. Mol. Biol. 3, 18, (1961)]. Two or more chromophores joined by various linker groups were shown to have much greater DNA and RNA affinity than the corresponding single chromophores. [King, H. D., Wilson, W. D. and Gabby, E., J. Biochem. 21, 4982. (1982)]. Diacridines in which the connecting paraffinic chain has six or more methylene groups have proved more effective in intercalation studies than those with fewer than six methylene groups. [Canellakis et al., Biochim. et al., Biophys. Acta., Volume 418, p. 277 (1976)]. Suitable diacridines for use in the present invention are those in which the two aromatic chromophores are connected by a paraffinic chain of three to ten carbon atoms length. Preferred diacridines are those separated by four to eight carbon atoms. More preferred are those separated by five to seven. Most preferred is the diacridine whose synthesis is described below, namely one in which the two chromophores are separated by a paraffinic chain of six carbon atoms length.

The silver staining method of the present invention for nucleic acids differs from the prior art in that the fixing step is a combination of fixing and chemical modification by inter or intra-strand intercalation, resulting in cross-linking. The cross-linked strands are retained preferentially in the matrix leading to greater sensitivity. This process of intercalation gives the present method its sensitivity advantage over other staining methods. The intercalating capacity of the fixing solution is responsible for enhanced sensitivity, particularly for low molecular weight nucleic acids. The most preferred intercalating agent, N,N'-di-(9-acridyl)-1,6-diaminohexane, has two acridinium moieties which are separated by a straight chain of six methylene groups, it is capable of interacting with two distinct DNA strands. This obviously helps retain smaller molecules in the matrix.

N,N'-Di-(9-acridyl)-1,6-diaminohexane can be prepared as follows:

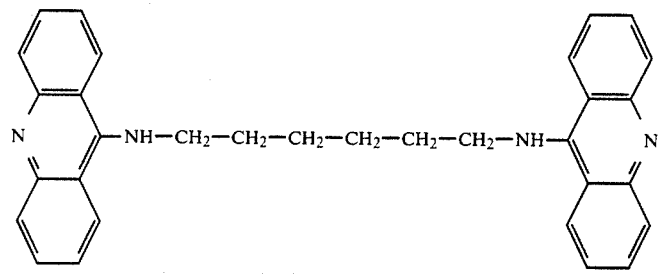

A solution of 21.35 g (0.1 mole) of 9-chloroacridine and 5.8 g (0.05 mole) of 1,6-diaminohexane in 100 mL of ethanol as refluxed for 2 hours under nitrogen. The reaction mixture was concentrated to one-third of the original volume and poured into 120 mL of 1M aqueous NaOH solution. The product was extracted with methylene chloride. The dried methylene chloride solution was evaporated to dryness, and the residue was crystallized from $EtOH/CHCl_3$ to give yellow crystals. M.P. was 178°–180° C. Yield was 67%.

We claim:

1. A kit for the optical detection of proteins and nucleic acids in a matrix, comprising:
   (a) a fixer comprising a compound selected from the group consisting of

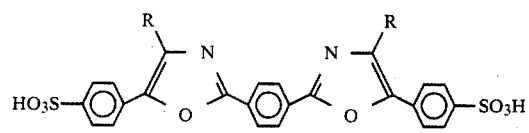

wherein R is H, $CH_3$, $C_2H_5$ or $CH_2N^+(CH_3)_3$,

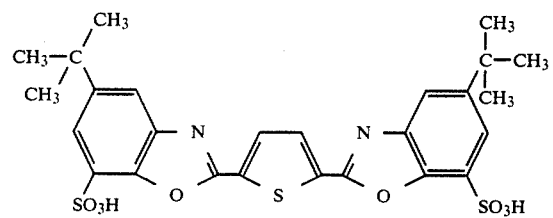

and

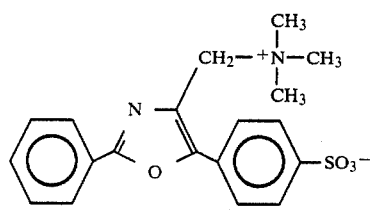

(b) a sensitizer selected from the group consisting of sodium sulfide, thiourea, dithiothreitol and sodium thiosulfate;
(c) a source of silver ions;

(d) a developer capable of reducing silver ions to metallic silver; and (e) a stopper capable of stopping reduction of silver ions to metallic silver.

2. The kit of claim 1 wherein the developer comprises sodium phosphate and formaldehyde.

3. The kit of claim 1 wherein the stopper comprises citric acid.

* * * * *